US00PP20741P2

(12) United States Plant Patent
Sahin-Georgiadou

(10) Patent No.: US PP20,741 P2
(45) Date of Patent: Feb. 9, 2010

(54) ***ACHILLEA* PLANT NAMED 'PINK GRAPEFRUIT'**

(50) Latin Name: *Achillea millefolium*
Varietal Denomination: Pink Grapefruit

(75) Inventor: Elisabeth Sahin-Georgiadou, Alphen aan den Rijn (NL)

(73) Assignee: K.Sahin Zaden B.V., Aalphen aan den Rijn (NL)

( * ) Notice: Subject to any disclaimer, the term of this patent is extended or adjusted under 35 U.S.C. 154(b) by 0 days.

(21) Appl. No.: 12/290,129

(22) Filed: Oct. 28, 2008

(51) Int. Cl.
*A01H 5/00* (2006.01)

(52) U.S. Cl. ..... Plt./263.1

(58) Field of Classification Search ..... Plt./263, Plt./263.1

See application file for complete search history.

*Primary Examiner*—Susan B McCormick Ewoldt
(74) *Attorney, Agent, or Firm*—C. A. Whealy

(57) ABSTRACT

A new and distinct cultivar of *Achillea* plant named 'Pink Grapefruit', characterized by its upright and mounding plant habit; strong and vigorous growth habit; freely flowering habit with plants remaining in flower for a long period time; inflorescences with dark pink-colored ray florets; and good garden performance.

1 Drawing Sheet

Botanical designation: *Achillea millefolium.*
Cultivar denomination: 'Pink Grapefruit'.

CROSS-REFERENCED TO RELATED APPLICATIONS:

Title: *Achillea* Plant Named 'Pomegranate'.
Applicant: Elisabeth Sahin-Georgiadou.
Filed: Concurrently with this application U.S. Plant patent application Ser. No. 12/290,128.
Title: *Achillea* Plant Named 'Saucy Seduction'.
Applicant: Elisabeth Sahin-Georgiadou.
Filed: Concurrently with this application U.S. Plant patent application Ser. No. 12/290,127.
Title: *Achillea* Plant Named 'Sunny Seduction'.
Applicant: Elisabeth Sahin-Georgiadou.
Filed: Concurrently with this application U.S. Plant patent application Ser. No. 12/290,126.

BACKGROUND OF THE INVENTION

The present invention relates to a new and distinct cultivar of *Achillea* plant, botanically known as *Achillea millefolium*, and hereinafter referred to by the name 'Pink Grapefruit'.

The new *Achillea* plant is a naturally-occurring whole plant mutation of *Achillea millefolium* 'Summer Pastels', not patented. The new *Achillea* plant was discovered and selected by the Inventor as a single flowering plant within a population of plants of 'Summer Pastels' in 2003 in a controlled outdoor nursery environment in Alphen aan den Rijn, The Netherlands. The selection of this plant was based on its unique inflorescence coloration.

Asexual reproduction of the new *Achillea* plant by vegetative cuttings in a controlled environment in Lancaster, Pa. since January, 2005, has shown that the unique features of this new *Achillea* plant are stable and reproduced true to type in successive generations.

SUMMARY OF THE INVENTION

Plants of the new *Achillea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Pink Grapefruit'. These characteristics in combination distinguish 'Pink Grapefruit' as a new and distinct cultivar of *Achillea:*

1. Upright and mounding plant habit.
2. Strong and vigorous growth habit.
3. Freely flowering habit with plants remaining in flower for a long period time.
4. Inflorescences with dark pink-colored ray florets.
5. Good garden performance.

Plants of the new *Achillea* differ from plants of the parent cultivar, 'Summer Pastels', in the following characteristics:

1. Plants of the new *Achillea* are more compact than and not as open as plants of 'Summer Pastels'.
2. Plants of the new *Achillea* have larger inflorescences than plants of 'Summer Pastels'.
3. Ray florets of plants of the new *Achillea* are dark pink in color whereas ray florets of 'Summer Pastels' are medium pink in color.

Plants of the new *Achillea* differ primarily in ray floret coloration from plants of *Achillea millefolium* 'Pomegranate', disclosed in a U.S. Plant patent application Ser. No. 12/290,128 filed concurrently; *Achillea millefolium* 'Saucy Seduction', disclosed in a U. S. Plant patent application Ser. No. 12/290,127 filed concurrently; and *Achillea millefolium* 'Sunny Seduction', disclosed in a U.S. Plant patent application Ser. No. 12/290,126 filed concurrently.

Plants of the new *Achillea* can also be compared to plants of *Achillea millefolium* 'Heidi', not patented. In side-by-side comparisons conducted in Lancaster, Pa., plants of the new *Achillea* differed from plants of 'Heidi' in the following characteristics:

1. Plants of the new *Achillea* were more upright than and not as open as plants of 'Heidi'.
2. Plants of the new *Achillea* were stronger and sturdier than plants of 'Heidi'.
3. Plants of the new *Achillea* and 'Heidi' differed in ray floret color.

BRIEF DESCRIPTION OF THE PHOTOGRAPHS

The accompanying photographs illustrate the overall appearance of the new *Achillea*. These photographs show the colors as true as it is reasonably possible to obtain in colored reproductions of this type. Colors in the photographs may differ slightly from the color values cited in the detailed botanical description which accurately describe the colors of the new *Achillea*.

The photograph at the bottom of the sheet comprises a side perspective view of a typical flowering plant of 'Pink Grapefruit' grown in a container.

The photograph at the top of the sheet is a close-up view of typical inflorescences of 'Pink Grapefruit'.

DETAILED BOTANICAL DESCRIPTION

Plants used for the aforementioned photographs and following observations and measurements describe plants grown in Lancaster, Pa. during the spring in one-gallon containers in a polyethylene-covered greenhouse and under conditions and practices which approximate those generally used in commercial *Achillea* production. During the production of the plants, day temperatures ranged from 18° C. to 27° C. and night temperatures ranged from 16° C. to 18° C. Measurements and numerical values represent averages for typical seven-month old flowering plants. In the following description, color references are made to The Royal Horticultural Society Colour Chart, 1995 Edition, except where general terms of ordinary dictionary significance are used.

Botanical classification: *Achillea millefolium* 'Pink Grapefruit'.

Parentage: Naturally-occurring whole plant mutation *Achillea millefolium* 'Summer Pastels', not patented.

Propagation:

*Type.*—Terminal vegetative cuttings.

*Time to initiate roots.*—About two to four days at 29° C.

*Time to produce a rooted cutting.*—About 12 to 14 days at 29° C.

*Root description.*—Medium in thickness, fleshy; white in color.

*Rooting habit.*—Freely branching; moderately dense.

Plant description:

*Plant form/growth habit.*—Upright and mounding plant habit. Strong and sturdy plants; vigorous growth habit.

*Plant height.*—About 40 cm.

*Plant diameter or spread.*—About 36 cm.

*Lateral branches.*—Quantity per plant: Freely branching habit with about 14 lateral branches developing per plant; pinching is typically not required. Length: About 36 cm. Diameter: About 4.5 mm. Internode length: About 2.5 cm. Aspect: Mostly upright. Strength: Strong, sturdy. Texture: Tomentose. Color: Close to 147C.

Foliage description:

*Arrangement.*—Alternate, simple; sessile.

*Length.*—About 8.6 cm.

*Width.*—About 2 cm.

*Shape.*—Lanceolate.

*Apex.*—Acute.

*Base.*—Truncate.

*Margin.*—Very finely dissected giving a fern-like and feathery appearance.

*Texture, upper and lower surfaces.*—Pubescent.

*Venation pattern.*—Pinnate.

*Color.*—Developing leaves, upper and lower surfaces: Close to 146A. Fully expanded leaves, upper and lower surfaces: Close to 146A; venation, close to 146B.

Inflorescence description:

*Flowering arrangement and habit.*—Rotate composite inflorescence form; inflorescences arranged in terminal or axillary compound cymes. Freely flowering habit with about 600 inflorescences developing per lateral branch. Inflorescences positioned above the foliage and face upright to outwardly.

*Fragrance.*—Faint; pungent.

*Time to flower.*—Long flowering period, under natural season conditions, plants flower throughout the summer; plants that are cut back will reflower.

*Post-production longevity.*—Inflorescences maintain good substance for about ten days on the plant; inflorescences persistent.

*Inflorescence bud.*—Height: About 5 mm. Diameter: About 3 mm. Shape: Ovoid. Color: Close to 155A.

*Cyme size.*—Diameter: About 6.2 cm by 8.5 cm. Height: About 5.2 cm.

*Inflorescence size.*—Diameter: About 1 cm. Depth (height): About 6 mm. Disc diameter: About 3 mm. Receptacle diameter: About 3 mm. Receptacle height: About 4 mm. Receptacle shape: Ovoid. Receptacle color: Close to 148B.

*Ray florets.*—Shape: Rounded obovate. Apex: Emarginate. Base: Attenuate. Length: About 6 mm. Width: About 4 mm. Margin: Entire. Texture, upper and lower surfaces: Smooth, glabrous. Number of ray florets per inflorescence: About five in a single whorl. Color: When opening, upper surface: Close to 69C to 69D. When opening, lower surface: Close to 155A. Fully opened, upper surface: Close to 72B; color becoming closer to 84A with development. Fully opened, lower surface: Close to 84C; color becoming close to 84D with development.

*Disc florets.*—Arrangement: Massed in the center of the receptacle. Shape: Tubular; apex, five-pointed. Length: About 5 mm. Diameter: About 1 mm. Number of disc florets per inflorescence: About 22. Color, immature: Apex: Close to 157A. Mid-section: Close to 145C. Base: Close to 145D. Color, mature: Apex: Close to 145D. Mid-section: Close to 145C. Base: Close to 145D.

*Phyllaries.*—Quantity per inflorescence: About 18 in about four whorls. Length: About 3 mm. Width: About 1.5 mm. Shape: Lanceolate. Apex: Acute. Base: Truncate, fused. Margin: Entire. Texture, upper surface: Smooth; glabrous. Texture, lower surface: Pubescent. Color, upper surface: Close to 145A. Color, lower surface: Close to 146D.

*Peduncles.*—Length, terminal peduncle: About 1.2 cm. Length, fourth peduncle: About 3.6 cm. Length, seventh peduncle: About 7 cm. Diameter: About 1.5 mm. Strength: Strong. Aspect: Mostly upright to about 45° from vertical. Texture: Pubescent. Color: Close to 147C.

*Reproductive organs* (*present on disc florets only*).—Androecium: Quantity of stamens per disc floret: About five. Filament length: About 2 mm. Filament color: Close to 145D. Anther shape: Rounded. Anther length: Less than 1 mm. Anther color: Close to 10C. Pollen amount: Scarce. Pollen color: Close to 10C. Gynoecium: Quantity of pistils per disc floret: One. Pistil length: About 5 mm. Stigma shape: Bi-parted. Stigma color: Close to 145D. Style length: About 2 mm. Style color: Close to 157A. Ovary color: Close to 157D.

*Seed/fruit.*—Seed and fruit production has not been observed.

Disease/pest resistance: Plants of the new *Achillea* have not been shown to be resistant to pathogens and pests common to *Achillea*.

Garden performance: Plants of the new *Achillea* have been observed to have good garden performance and tolerate wind, rain and temperatures ranging from about −20° C. to about 40° C.

It is claimed:

1. A new and distinct *Achillea* plant named 'Pink Grapefruit' as illustrated and described.

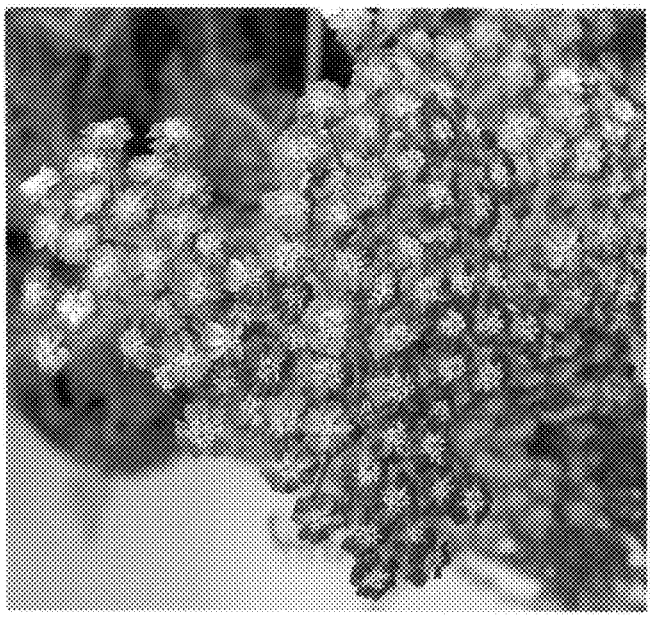
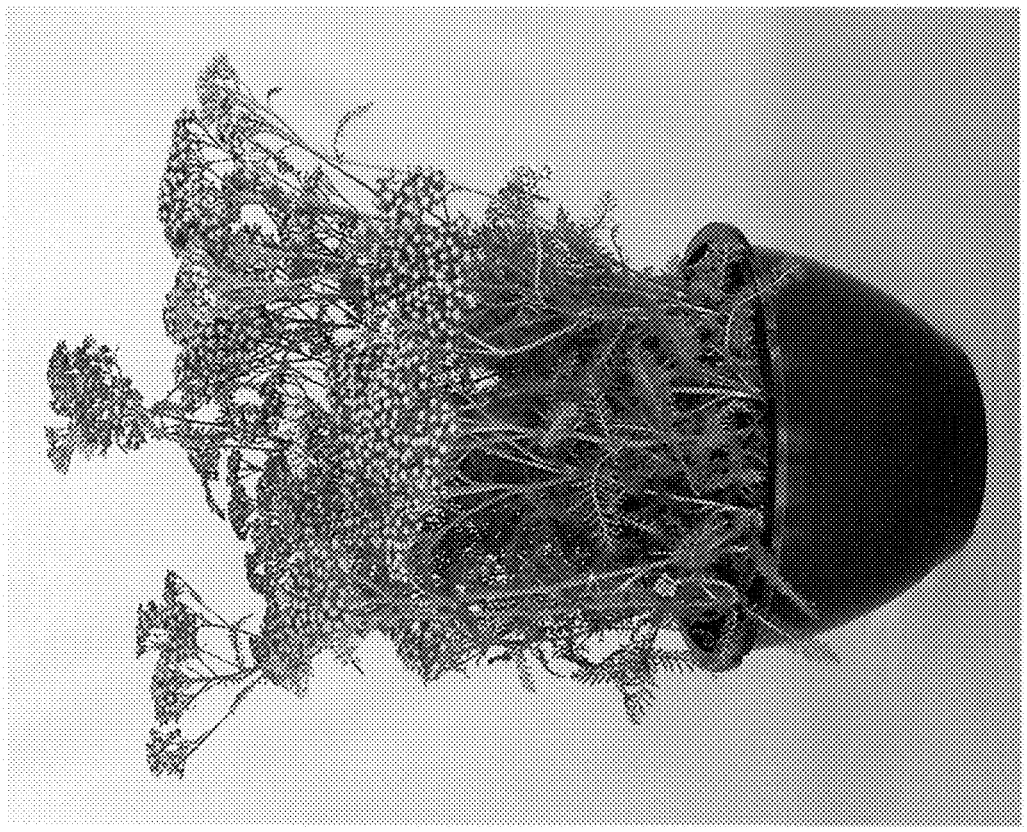

* * * * *